United States Patent [19]

Rehr et al.

[11] Patent Number: 5,102,795
[45] Date of Patent: Apr. 7, 1992

[54] PROCESS FOR OBTAINING SORBITOL AND GLUCONIC ACID OR GLUCONATE

[75] Inventors: Bert Rehr; Hermann Sahm, both of Juelich, Fed. Rep. of Germany

[73] Assignee: Forschungszentrum Juelich GmbH, Juelich, Fed. Rep. of Germany

[21] Appl. No.: 606,821

[22] Filed: Oct. 31, 1990

[30] Foreign Application Priority Data

Nov. 4, 1989 [DE] Fed. Rep. of Germany ....... 3936757

[51] Int. Cl.$^5$ .......................... C12P 7/18; C12P 7/58; C12N 1/20; C12N 1/38
[52] U.S. Cl. .................................. 435/137; 435/158; 435/176; 435/177; 435/182; 435/244; 435/253.6; 435/259; 435/822
[58] Field of Search ............... 435/137, 158, 176, 177, 435/182, 822, 259, 244, 253.6

[56] References Cited

U.S. PATENT DOCUMENTS 4,775,467 7/1988 Scopes et al. ................. 435/125
5,017,485 5/1991 Bringer-Meyer et al. ......... 435/158

FOREIGN PATENT DOCUMENTS 0212517 3/1987 European Pat. Off. .
0250407 1/1988 European Pat. Off. .
0322723 7/1989 European Pat. Off. .

OTHER PUBLICATIONS

H. Felix, "Analytical Biochemistry", *Permeabilized Cells*, 1982, pp. 211–234.
Reiff et al., "Yeasts in Science", *Yeasts, vol. I, 1960*, pp. 301–302.

*Primary Examiner*—Herbert J. Lilling
*Attorney, Agent, or Firm*—Foley & Lardner

[57] ABSTRACT

A process for obtaining sorbitol and gluconic acid or gluconate from aqueous glucose/fructose mixtures by using *Zymomonas mobilis* cells which have been permeabilized by treatment with cationic surfactant is disclosed. The permeabilized cells are preferably obtained by treatment with long-chain quaternary alkylammonium salts such as, in particular, CTAB, Dodigen or Bardac. Surfactant concentrations of 0.1 to 0.3% and a treatment time of 1 to 10 minutes at room temperature are expedient. The cell concentrations preferably used for the fermentation are 20 to 80 g/l dry matter of permeabilized cells.

12 Claims, No Drawings

PROCESS FOR OBTAINING SORBITOL AND GLUCONIC ACID OR GLUCONATE

BACKGROUND OF THE INVENTION

The present invention relates to a process for obtaining sorbitol and gluconic acid or gluconate from aqueous glucose/fructose mixtures by conversion in the presence of permeabilized cells of *Zymomonas mobilis*, and also to cells which can be used for the process.

It is known that sorbitol and gluconic acid or gluconate are produced in aqueous glucose/fructose mixtures enzymatically using glucose dehydrogenase and sorbitol dehydrogenase in the simultaneous presence of cofactors. Continuous addition or regeneration of the cofactors is a requirement for this process.

Thus, a process for the microbial conversion of glucose and fructose in aqueous solution using bacteria containing glucose/fructose transhydrogenase and, in particular, *Zymomonas mobilis*, has already been developed and is described in U.S. Pat. No. 4,755,467. This process uses desalted cell-free extracts, immobilized cells or non-growing cells which have been washed with phosphate, free buffer and which have, where appropriate, been permeabilized by a toluene treatment in 10% strength (v/v) toluene solution. As an alternative, gluconate kinase-negative mutants are produced and used.

Although a toluene treatment of this type results in premeabilized cells which are very useful for the desired fermentation, it appears non-optimal to use such considerable quantities of tulene for the permeabilization, ant there also appears to be a considerable risk that toluene residues may remain in the cell material.

SUMMARY OF THE INVENTION

It is therefore an object of the present invention to provide a process for conversion using permeabilized cells which can be obtained reproducibly with small amounts of foreign substances and from which remaining residues can easily be removed.

In accomplishing these and other objects according to the invention, a process for obtaining sorbitol and gluconic acid or gluconate starting from an aqueous glucose/fructose mixtures has been provided, comprising the steps of permeabilizing cells of *Zymomonas mobilis* with a cationic surfactant, and converting an aqueous glucose/fructose mixture to sorbitol and gluconic acid or gluconate with said permeabilized cells. Permeabilized *Zymomonas mobilis* cells obtained by treatment with cationic surfactant are provided for practice of the process. In a preferred embodiment, these permeabilized cells are immobilized on a carrier material.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

The process according to the invention comprises the use of cells permeabilized by treatment with a cationic surfactant. The cationic surfactant used for this purpose is preferably a long-chain quaternary alkylammonium compound, in particular one represented by the formula I

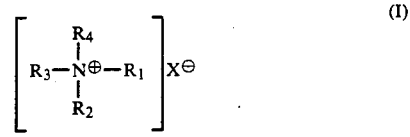

in which at least one of the radicals $R_1$ to $R_4$ is a hydrocarbon radical with at least 8 C atoms, while the other R radicals can be identical or different and are each lower alkyl, especially $CH_3$ or, where appropriate, $C_6H_5$—$CH_2$, and x is a compatible anion, especially chloride or bromide.

Particularly expedient cationic surfactants corresponding to the formula I are those in which $R_1$ and, where appropriate, $R_2$ is an alkyl radical with 10 to 16 C atoms and the other R radicals are $CH_3$ groups, one of which can carry a phenyl radical, and X is chloride or bromide.

Dodigen ®(dodecyldimethylbenzylammonium chloride), Bardac ®(didecyldimethylammonium chloride) and cetyltrimethylammonium bromide (CTAB) and chloride belong to this group and are commercially-available cationic surfactants. Because of their availability, these were investigated more extensively, especially cetyltrimethylammonium bromide (CTAB).

Although the use of detergents for permeabilizing cells generally has been known for some time, as reported in the review article by H. Felix (*Analytical Biochemistry* 120:211-23 (1982)), which mentions CTAB, the review shows that non-ionic detergents have been mainly employed to date.

It has now been discovered that cationic surfactants are particularly useful for treatment of *Zymomonas mobilis*, that they can be used in especially small amounts, and that they lead to optimal permeabilization. Comparative tests carried out with various detergents demonstrate the unexpected superiority of cationic detergents.

For this purpose, freshly cultured cells were suspended in 0.1 N sodium citrate buffer (pH 6.4) in amounts of 20 to 30 g/l (dry weight; final concentration generally amounts up to 80 g/l are convenient and the cell suspension was mixed with detergent solution for a final concentration of 0.1% (CTAB, Dodigen and Bardac) or 1% (other surfactants) or 10% (toluene). After incubation for b 10 minutes, the cells were centrifuged and washed twice with sodium citrate buffer to remove residues of surfactant or toluene.

The cells permeabilized in this way were used for the conversion of aqueous glucose/fructose mixtures, and the concentration of glucose-6-phosphate dehydrogenase (glucose-6-P DH) was measured to check the success of permeabilization. In this regard, glucose-6-P DH serves as a marker enzyme. The activity of this intracellular enzyme can be measured only where cells have been disrupted or permeabilized, because the cell membrane of intact cells is impermeable to the NADH present in the measurement mixture.

The activities indicated in the following Table 1 are means from 7 measurements in each case with two different cell harvests. The zero value was obtained with untreated cell material. Ultrasonically-disrupted cell material is referred to as crude extract.

TABLE 1

Permeabilization of Z. mobilis with toluene and various detergents

| Treatment with | Conc. % | μmol sorbitol/mg protein × min | μmol gluconate/mg protein × min | Glucose-6-P DH in μmol NADH/mg protein × min |
|---|---|---|---|---|
| 0 value | | 0.2 | 0.2 | 0.25 |
| Crude extract | | 0.28 | 0.28 | 2.3 |
| CTAB | 0.1 | 0.23 | 0.2 | 2.0 |
| *Dodigen 1611 | 0.1 | 0.18 | 0.18 | 2.0 |
| **Bardac 22 | 0.1 | 0.21 | 0.21 | 1.9 |
| Tween 80 | 1 | 0.18 | 0.2 | 0.8 |
| Brij 58 | 1 | 0.2 | 0.2 | 0.5 |
| Nonidet-P 40 | 1 | 0.22 | 0.22 | 0.9 |
| Lubrol Px | 1 | 0.23 | 0.22 | 1.2 |
| Toluene | 10 | 0.23 | 0.22 | 1.8 |

*Dodecyldimethylbenzylammonium chloride
**Didecyldimethylammonium chloride

The data show that optimal permeabilization is achieved with quaternary ammonium salts. This is particularly evident from the last column, which shows that the amount of marker enzyme in the case of cells treated with CTAB, Dodigen or Bardac is of the order of magnitude of that of the crude extract, while the value for the marker enzyme is distinctly lower with the other detergents. The higher measurement for the marker enzyme shows greater permeability of the cell membrane. As the permeability of the cell membrane increases, the cofactors which are important for cellular metabolism, such as AND, ATP, etc., are able to leave the cell more rapidly and completely so that fermentation of glucose and fructose to ethanol and $CO_2$ and degradation of gluconic acid, are no longer possible. This means that a maximum product yield is achieved long-term. Thus, the comprehensive permeabilization results in a product yield which is not reduced by ethanol production.

The surfactant concentrations particularly preferred for the permeabilization treatment are from about 0.1 to 0.3%, and the treatment time is, in particular, about 1 to 10 minutes at room temperature, as is evident from the following optimization tests.

A) ALTERATION IN THE CTAB CONCENTRATION

The procedure indicated above for the comparative tests was repeated using different CTAB concentrations. The results are shown in Table 2.

TABLE 2

Permeabilization of Z. mobilis with various concentrations of CTAB. The incubation time (treatment with detergent) was 10 minutes.

| CTAB (%) | Glucose-6-P DH in μmol NADH/mg protein × min |
|---|---|
| 0 | 0.15 |
| 0.05 | 0.26 |
| 0.1 | 1.75 |
| 0.2 | 1.8 |

B) ALTERNATION IN THE TREATMENT TIMES

Analogous tests were carried out altering the treatment time. The results of these are compiled in Table 3 which follows.

TABLE 3

Effect of the incubation time on the permeabilization of Z. mobilis with CTAB. The CTAB concentration was 0.1%.

| Incubation time | Glucose-6-P DH in μmol NADH/mg protein × min |
|---|---|
| without CTAB | 0.12 |
| 1 min | 1.8 |
| 2.5 min | 1.68 |
| 5 min | 1.72 |
| 10 min | 1.75 |

The data show that concentrations below about 0.1% CTAB are insufficient to produce adequate permeabilization. No further improvement is achieved by increasing the concentration above about 0.3%. While the data show that permeabilization is attained within one minute, it appears expedient to employ a somewhat longer treatment time of up to about 10 minutes, particularly with large batches in order to avoid local variations owing to inadequate mixing in larger batches.

Examples of the preparation of sorbitol and gluconic acid using the permeabilized cells according to the invention follow.

CONVERSION OF GLUCOSE AND FRUCTOSE INTO SORBITOL AND GLUCONIC ACID IN A SMALL FERMENTER WITH VARIOUS SUGAR CONCENTRATIONS USING INTACT AND CTAB-PEREMABILIZED CELLS

The conversion was carried out at 39° C. under static pH conditions (0.1 M sodium citrate buffer pH 6.4; titrated with 3 N NaOH).

| A. Conversion with intact cells, substrate concentration 123 g/l for both fructose and glucose, cell concentration 22.1 g/l protein. | |
|---|---|
| Time for conversion: | 3 hours |
| Sorbitol: | 107 g/l (conversion efficiency: 85.9%) |
| Gluconic acid: | 77 g/l (conversion efficiency: 57.5%) |
| Fructose: | 30 g/l |
| Glucose: | 0 g/l |
| Ethanol produced: | 21 g/l |
| B. Conversion with CTAB-permeabilized cells, substrate concentration 105 g/l for both fructose and glucose, cell concentration 14.4 g/l protein. | |
| Time for conversion: | 9.5 hours |
| Sorbitol: | 103 g/l (conversion efficiency: 97%) |
| Gluconic acid: | 110 g/l (conversion efficiency: 99%) |
| Glucose and fructose: | 0 g/l |
| Ethanol produced: | ≦0.8 g/l |
| C. Conversion with CTAB-permeabilized cells, substrate concentration 200 g/l fructose and 194 g/l glucose, cell concentration 23.3 g/l protein. | |
| Time for conversion: | 6 hours |
| Sorbitol: | 200 g/l (conversion efficiency: 99%) |
| Gluconic acid: | 209 g/l (conversion efficiency: 99%) |
| Glucose and fructose: | 0 g/l |
| Ethanol produced: | ≦0.8 g/l |

-continued

D. Conversion with CTAB-permeabilized cells, substrate concentration 292 g/l fructose and 281 g/l glucose, cell concentration 39.6 g/l protein.

| Time for conversion: | 6 hours |
|---|---|
| Sorbitol: | 285 g/l (conversion efficiency: 97.0%) |
| Gluconic acid: | 295 g/l (conversion efficiency: 96.5%) |
| Glucose and fructose: | 0 g/l |
| Ethanol produced: | ≦0.8 g/l |

The results obtained are compiled in Table 4 which follows.

TABLE 4

Comparative kinetic data expressed as maximum productivities in g of product/hour × g of protein

| Cell material | g sorbitol h × g | Yield (%) | g gluconic acid h × g | Yield (%) |
|---|---|---|---|---|
| Intact cells | 2.2 | 85.9 | 2.1 | 57.5 |
| CTAB cells, see under B. | 3.2 | 97 | 3.3 | 99 |
| CTAB cells, see under C. | 3.7 | 98 | 3.8 | 99 |
| CTAB cells, see under D. | 3.4 | 97.0 | 3.4 | 96.5 |

It is apparent that permeabilization with CTAB leads to an increase in product yield and achievement of maximum productivities (conversion rate). Ethanol production is minimized when permeabilized cells are used, so that no loss of yield of desired product owing to such byproduct formation is observed.

The concentrations of permeabilized cells used for the conversion are about 20–80 g/l cell dry matter (corresponding to about 10–40 g/l protein). The permeabilized cells can be stored and made commercially available.

The permeabilized cells can be used in immobilized form, which permits the process to be carried out continuously. In this context, the cell material may be attached by adsorption or covalently attached to an inorganic or organic carrier. The carrier can be in finely divided or fragmentary form or as shaped article. The cells can also be used entrapped in a porous matrix.

Retention of the cells in a reactor using microporous membranes is also possible, as is removal, for example, by microfiltration, from the reactor discharge, with the removed cells being returned to the reactor.

What is claimed is:

1. A process for obtaining sorbitol and gluconic acid or gluconate starting from an aqueous glucose/fructose mixtures, comprising the steps of:
   permeabilizing cells of *Zymomonas mobilis* with a cationic surfactant; and
   converting an aqueous glucose/fructose mixture to sorbitol and gluconic acid or gluconate with said permeabilized cells.

2. The process as claimed in claim 1, wherein the cationic surfactant is a long-chain quaternary alkylammonium compound.

3. The process as claimed in claim 2, wherein the cationic surfactant is a compound of the formula (I)

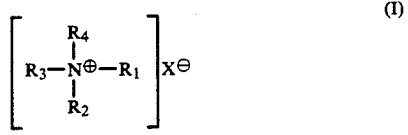

in which at least one of the radicals $R_1$ to $R_4$ is a hydrocarbon radical with at least 8 C atoms, the remaining R radicals are identical or different and are each one member of the group lower alkyl and benzyl and X is a compatible anion.

4. The process as claimed in claim 3, wherein at least one of the radicals $R_1$ and $R_2$ is an alkyl radical with 10 to 16 atoms and the other R radicals are $CH_3$ groups and X is chloride or bromide.

5. The process as claimed in claim 1, wherein an about 0.1 to 0.3% strength surfactant solution at room temperature for 1 to 10 minutes is used in said permeabilizing step and the cells are washed to remove excess surfactant.

6. The process as claimed in claim 1, wherein said converting step is carried out using permeabilized cells in concentrations of about 20 to 80 g/l of cell dry matter.

7. The process as claimed in claim 3, wherein said lower alkyl means $CH_3$.

8. The process as claimed in claim 3, wherein X is chloride or bromide.

9. The process as claimed in claim 4, wherein one of the R radicals is $CH_3$ substituted by a phenyl group.

10. The process as claimed in claim 3, wherein $R_1$ and $R_2$ are alkyl radicals with 10 to 16 atoms.

11. The process as claimed in claim 1, wherein the converting step is a conversion of aqueous fructose into sorbitol.

12. The process as claimed in claim 1, wherein the converting step is a conversion of aqueous glucose into gluconate or gluconic acid.

* * * * *